United States Patent
Ikeda et al.

(10) Patent No.: US 7,429,425 B2
(45) Date of Patent: Sep. 30, 2008

(54) OLIGOARYLENE DERIVATIVES AND ORGANIC ELECTROLUMINESCENT DEVICES MADE BY USING THE SAME

(75) Inventors: Hidetsugu Ikeda, Sodegaura (JP); Masahide Matsuura, Sodegaura (JP); Hisayuki Kawamura, Sodegaura (JP)

(73) Assignee: Idemitsu Kosan Company, Ltd., Tokyo (JP)

( * ) Notice: Subject to any disclaimer, the term of this patent is extended or adjusted under 35 U.S.C. 154(b) by 442 days.

(21) Appl. No.: 10/522,546

(22) PCT Filed: Aug. 7, 2003

(86) PCT No.: PCT/JP03/10071

§ 371 (c)(1),
(2), (4) Date: Jan. 27, 2005

(87) PCT Pub. No.: WO2004/016575

PCT Pub. Date: Feb. 26, 2004

(65) Prior Publication Data

US 2006/0134456 A1     Jun. 22, 2006

(51) Int. Cl.
*H01L 51/54*    (2006.01)
*C09K 11/06*    (2006.01)
*C07C 13/32*    (2006.01)

(52) U.S. Cl. .......................... 428/690; 585/27; 428/917; 313/504; 313/506; 257/40; 257/E51.028; 257/E51.049

(58) Field of Classification Search .................. None
See application file for complete search history.

(56) References Cited

U.S. PATENT DOCUMENTS

| | | | | |
|---|---|---|---|---|
| 3,121,122 A | * | 2/1964 | Reimlinger | 585/26 |
| 3,711,567 A | * | 1/1973 | Innes | 585/26 |
| 5,935,721 A | * | 8/1999 | Shi et al. | 428/690 |
| 2003/0072966 A1 | * | 4/2003 | Hosokawa et al. | 428/690 |

FOREIGN PATENT DOCUMENTS

| | | |
|---|---|---|
| EP | 1 191 822 | 3/2002 |
| JP | 03-200889 | 9/1991 |
| JP | 07-138561 | 5/1995 |
| JP | 08-239655 | 9/1996 |
| JP | 2000 012229 | 1/2000 |
| JP | 2000-273055 | * 3/2000 |
| JP | 2000 273056 | 10/2000 |
| JP | 2001 118682 | 4/2001 |
| JP | 2001 118683 | 4/2001 |
| JP | 2001 257075 | 9/2001 |
| JP | 2001 332384 | 11/2001 |
| JP | 2001-335516 | 12/2001 |
| WO | WO 2000/039247 | * 6/2000 |

OTHER PUBLICATIONS

Machine translation of JP 2000-012229, Maki et al.*
Machine translation of JP 2002-063988, Kohama et al.*
Marvel et al., Journal of the American Chemical Society, (1939), vol. 61, pp. 895-897.*
Machine Assisted Translation, JP 2000-273055, Ikeda et al.*
Arikainen, E. et al, "Complimentary Polytopic Interactions," Angew, Chem. Int. Ed., vol. 39, No. 13, 2000, pp. 2333-2336.
Patent Abstracts of Japan, JP 2002-63988 A (Toray Industries, Inc.), Feb. 28, 2002.
Patent Abstracts of Japan, JP 2000-273055 A (Idemitsu Kosan Co., Ltd.), Oct. 3, 2000.
Chihaya Adachi, et al., "Blue light-emitting organic electroluminescent devices," Appl. Phys. Lett., vol. 56, No. 9, Feb. 26, 1990, pp. 799-801.
C.W. Tang, et al., "Organic electroluminescent diodes," Appl. Phys. Lett., vol. 51, No. 12, Sep. 21, 1987, pp. 913-915.

* cited by examiner

*Primary Examiner*—Gwendolyn Blackwell
*Assistant Examiner*—Brett A Crouse
(74) *Attorney, Agent, or Firm*—Steptoe & Johnson LLP

(57) ABSTRACT

There are provided oligoarylene derivatives capable of emitting blue light at high luminous efficiency which are represented by the following general formulae (1) to (4):

$$Ar^1\text{-Ch-}Ar^2 \quad (1)$$

$$Ch^1\text{-L-}Ch^2 \quad (2)$$

$$Ar^3\text{-}(L^1)_a\text{-}Ch^3\text{-}(L^2)_b\text{-}Ar^4 \quad (3)$$

$$Ar^5\text{-}Ch^4\text{-}(Ar^7)_n\text{-}L^3\text{-}(Ar^8)_m\text{-}Ch^5\text{-}Ar^6 \quad (4)$$

wherein Ch, $Ch^1$ and $Ch^2$ are respectively a group containing at least one substituted or unsubstituted condensed aromatic ring having 14 to 20 nuclear atoms; $Ch^3$, $Ch^4$ and $Ch^5$ are respectively a substituted or unsubstituted arylene group having 14 to 20 nuclear atoms; $Ar^1$, $Ar^2$, $Ar^3$, $Ar^4$, $Ar^5$ and $Ar^6$ are respectively a substituted or unsubstituted aryl group having 5 to 30 nuclear atoms; $Ar^7$ and $Ar^8$ are respectively a substituted or unsubstituted arylene group having 5 to 30 nuclear atoms; $L^1$, $L^2$ and $L^3$ are respectively a connecting group; and a, b, n and m are respectively an integer of 0 to 1, as well as organic electroluminescent devices using the same.

11 Claims, No Drawings

OLIGOARYLENE DERIVATIVES AND ORGANIC ELECTROLUMINESCENT DEVICES MADE BY USING THE SAME

TECHNICAL FIELD

The present invention relates to oligoarylene derivatives and organic electroluminescent devices made by using the same, and more particularly to oligoarylene derivatives capable of emitting blue light at a high luminous efficiency and organic electroluminescent devices made by using the same.

BACKGROUND ART

The organic electroluminescent devices (hereinafter, "electroluminescent" is referred to merely as "EL") are emitting devices using the principle that a phosphor or fluorescent substance emits light by an energy of recombination between holes injected from an anode and electrons injected from a cathode upon application of an electric field thereto. Since C. W. Tang, et al., of Kodak Company have reported low-voltage drive organic EL devices of a laminated type (C. W. Tang and S. A. Vanslyke, "Applied Physics Letters", Vol. 51, p. 913, 1987, etc.), there have been made intense studies concerning organic EL devices made of organic materials. The organic EL devices reported by Tang, et al., include a luminescent layer made of tris(8-hydroxyquinolinol)aluminum and a hole transport layer made of a triphenyl diamine derivative. The laminated structure of these devices provides advantages such as enhanced injection efficiency of holes into the luminescent layer, enhanced production efficiency of excitons that are produced by blocking electrons injected from a cathode and recombining the electrons with holes, and confinement of the excitons produced within the luminescent layer. As the structure of such organic EL devices, there are well known a two-layer structure including a hole transport (injection) layer and an electron transport luminescent layer, a three-layer structure including a hole transport (injection) layer, a luminescent layer and an electron transport (injection) layer, etc. In these organic EL devices of a laminated type, various structures and methods for production thereof have been proposed in order to enhance an efficiency of recombination between holes and electrons injected.

In addition, as the luminescent materials for the above devices, there are known chelate complexes such as tris(8-quinolinolato) aluminum complexes, coumarin derivatives, tetraphenyl butadiene derivatives, bis-styryl arylene derivatives and oxadiazole derivatives. It has been reported that these luminescent materials emit blue to red light in a visible range, and it is therefore expected to apply these luminescent materials to production of color display devices (for example, Japanese Patent Application Laid-open Nos. Hei 8(1996)-239655, Hei 7(1995)-138561 and Hei 3(1991)-200889, etc.).

However, there exist few blue emitting luminescent materials capable of providing highly-reliable and stable blue light-emitting devices. In general, the conventional blue emitting luminescent materials are easy to crystallize. For example, diphenyl anthracene shows a high crystallinity nevertheless their high fluorescent quantum yield. Therefore, the use of such a compound as a luminescent material has failed to provide devices exhibiting a high luminous efficiency and a high reliability (C. Adachi, et al., "Applied Phys. Lett.", 56, 799 (1990)).

DISCLOSURE OF THE INVENTION

The present invention has been made for solving the above conventional problems. An object of the present invention is to provide oligoarylene derivatives capable of emitting blue light at a high luminous efficiency as well as organic EL devices made by using the compounds.

As a result of extensive researches for accomplishing the above object, the inventors have found that organic EL devices made by using the oligoarylene derivatives represented by the following general formulae (1) to (4) as a luminescent material or a hole transport material therefor are capable of emitting blue light at a high luminous efficiency.

The present invention has been accomplished on the basis of the above finding.

Thus, the present invention provides an oligoarylene derivative represented by any of the following general formulae (1) to (4):

$$Ar^1\text{-Ch-}Ar^2 \qquad (1)$$

wherein Ch is a group containing at least one substituted or unsubstituted condensed aromatic ring having 14 to 20 nuclear carbon atoms; and $Ar^1$ and $Ar^2$ are respectively a substituted or unsubstituted aryl group having 5 to 30 nuclear atoms and may be the same or different from each other,

$$Ch^1\text{-L-}Ch^2 \qquad (2)$$

wherein L is a connecting group; and $Ch^1$ and $Ch^2$ are respectively a group containing at least one substituted or unsubstituted condensed aromatic ring having 14 to 20 nuclear carbon atoms and may be the same or different from each other,

$$Ar^3\text{-}(L^1)_a\text{-}Ch^3\text{-}(L^2)_b\text{-}Ar^4 \qquad (3)$$

wherein $Ch^3$ is a substituted or unsubstituted arylene group having 14 to 20 nuclear carbon atoms;

$L^1$ and $L^2$ are respectively a connecting group and may be the same or different from each other; a and b are respectively an integer of 0 to 1; and $Ar^3$ and $Ar^4$ are respectively a substituted or unsubstituted aryl group having 5 to 30 nuclear atoms and may be the same or different from each other with the proviso that when $Ch^3$ is a substituted or unsubstituted pyrene residue, $Ar^3$ and/or $Ar^4$ are respectively a substituted or unsubstituted β-naphthyl derivative, and

$$Ar^5\text{-}Ch^4\text{-}(Ar^7)_n\text{-}L^3\text{-}(Ar^8)_m\text{-}Ch^5\text{-}Ar^6 \qquad (4)$$

wherein $L^3$ is a connecting group; $Ch^4$ and $Ch^5$ are respectively a substituted or unsubstituted arylene group having 14 to 20 nuclear atoms and may be the same or different from each other;

$Ar^5$ and $Ar^6$ are respectively a substituted or unsubstituted aryl group having 5 to 30 nuclear atoms and may be the same or different from each other;

$Ar7$ and $Ar^8$ are respectively a substituted or unsubstituted arylene group having 5 to 30 nuclear atoms and may be the same or different from each other; and n and m are respectively an integer of 0 to 1.

Also, the present invention provides an organic electroluminescent device comprising a cathode, an anode and an organic thin film layer sandwiched between the cathode and the anode which is constituted of a single layer or a plurality of layers including at least one luminescent layer, wherein at least one layer of the organic thin film layer contains the oligoarylene derivative represented by any of the general formulae (1) to (4) as a single component or a component of a mixture.

BEST MODE FOR CARRYING OUT THE INVENTION

The oligoarylene derivative of the present invention is represented by the following general formula (1) or (2).

(1)

In the general formula (1), Ch is a group containing at least one substituted or unsubstituted condensed aromatic ring having 14 to 20 nuclear carbon atoms.

Examples of the condensed aromatic ring represented by Ch include phenanthrene, pyrene, chrysene, triphenylene and perylene. Of these condensed aromatic rings, preferred are pyrene and chrysene.

$Ar^1$ and $Ar^2$ are respectively a substituted or unsubstituted aryl group having 5 to 30 nuclear atoms, and may be the same or different from each other.

Examples of the substituted or unsubstituted aryl group having 5 to 30 nuclear atoms which is represented by $Ar^1$ and $Ar^2$ include phenyl, 1-naphthyl, 2-naphthyl, 1-anthryl, 2-anthryl, 9-anthryl, 1-phenathryl, 2-phenathryl, 3-phenathryl, 4-phenathryl, 9-phenathryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl and fluorenyl.

(2)

In the general formula (2), L is a connecting group. Example of the connecting group include groups having a structure of a single bond, methylene, ethylene, dimethylmethylene, diphenylmethylene, lactone ring or peptide. Of these connecting groups, preferred is a single bond. These groups may have substituent groups.

Examples of the condensed aromatic rings represented by $Ch^1$ and $Ch^2$ are the same as those condensed aromatic rings represented by the above Ch.

The above general formula (1) is preferably represented by the general formula (3).

In the general formula (3), $Ch^3$ is a substituted or unsubstituted arylene group having 14 to 20 nuclear carbon atoms. Examples of the arylene group represented by $Ch^3$ include divalent residues of phenanthrene, pyrene, chrysene, triphenylene and perylene. Of these arylene groups, preferred are divalent residues of pyrene and chrysene.

$L^1$ and $L^2$ are respectively a connecting group and may be the same or different from each other. Examples of the connecting groups represented by $L^1$ and $L^2$ are the same as those connecting groups represented by the above L. These connecting groups may have substituent groups. The symbols a and b are respectively an integer of 0 to 1.

Ar3 and $Ar^4$ are respectively a substituted or unsubstituted aryl group having 5 to 30 nuclear atoms, and may be the same or different from each other. Examples of the aryl group are the same as those represented by the above $Ar^1$ and $Ar^2$.

However, when $Ch^3$ is a substituted or unsubstituted pyrene residue, $Ar^3$ and/or $Ar^4$ are respectively a substituted or unsubstituted β-naphthyl derivative.

The above general formula (2) is preferably represented by the general formula (4).

In the general formula (4), $L^3$ is a connecting group. Examples of the connecting group represented by $L^3$ are the same as those connecting groups represented by the above L. The connecting group may have substituent groups.

$Ch^4$ and $Ch^5$ are respectively a substituted or unsubstituted arylene group having 14 to 20 nuclear atoms, and may be the same or different from each other. Examples of the arylene group include phenanthrylene, pyrenylene, chrysenylene, triphenylenylene and perylenylene. Of these arylene groups, preferred are pyrenylene and chrysenylene.

$Ar^5$ and $Ar^6$ are respectively a substituted or unsubstituted aryl group having 5 to 30 nuclear atoms and may be the same or different from each other. Examples of the aryl group are the same as those groups represented by the above $Ar^1$ and $Ar^2$.

$Ar^7$ and $Ar^8$ are respectively a substituted or unsubstituted arylene group having 5 to 30 nuclear atoms and may be the same or different from each other. Examples of the arylene group are divalent groups of the aryl groups represented by the above $Ar^1$ and $Ar^2$. The symbols n and m are respectively an integer of 0 to 1.

Examples of the substituent groups of the above groups represented by Ch, $Ch^1$ to $Ch^5$ and $Ar^1$ to $Ar^8$ include halogen atoms, hydroxyl, nitro, cyano, alkyl, aryl, cycloalkyl, alkoxy, aromatic heterocyclic groups, aralkyl, aryloxy, arylthio, alkoxycarbonyl and carboxyl.

Examples of the substituent groups of the groups represented by the above L and $L^1$ to $L^3$ are also the same as described above.

Specific examples of the oligoarylene derivatives represented by the above general formulae (1) to (4) are as follows, though they are not limited to these compounds.

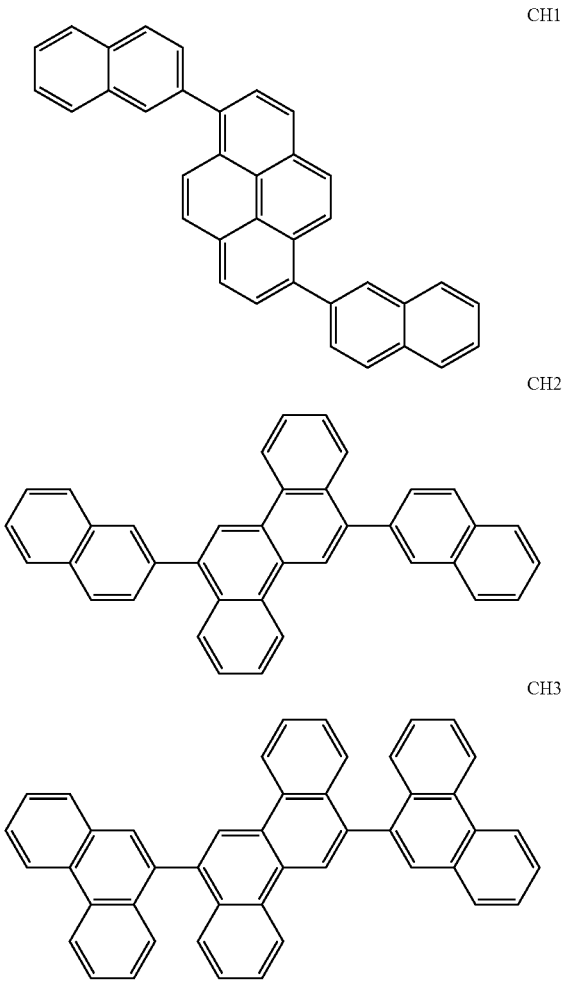

-continued
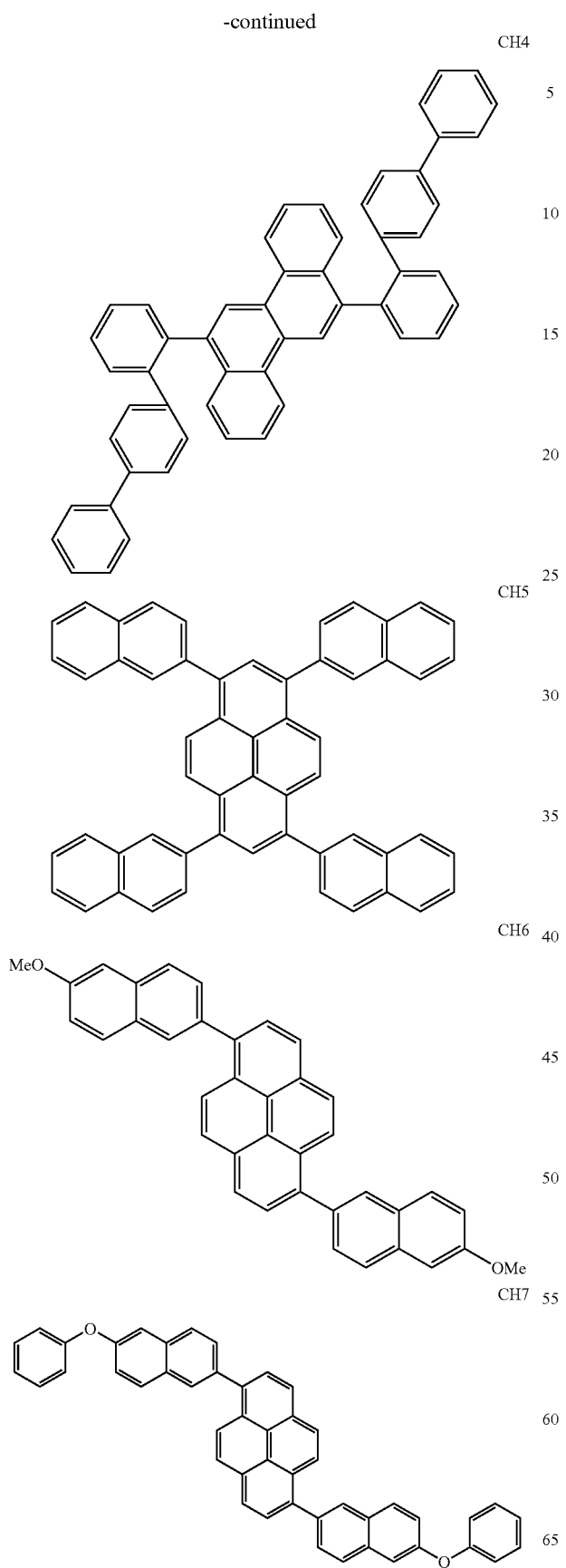
CH4
CH5
CH6
CH7
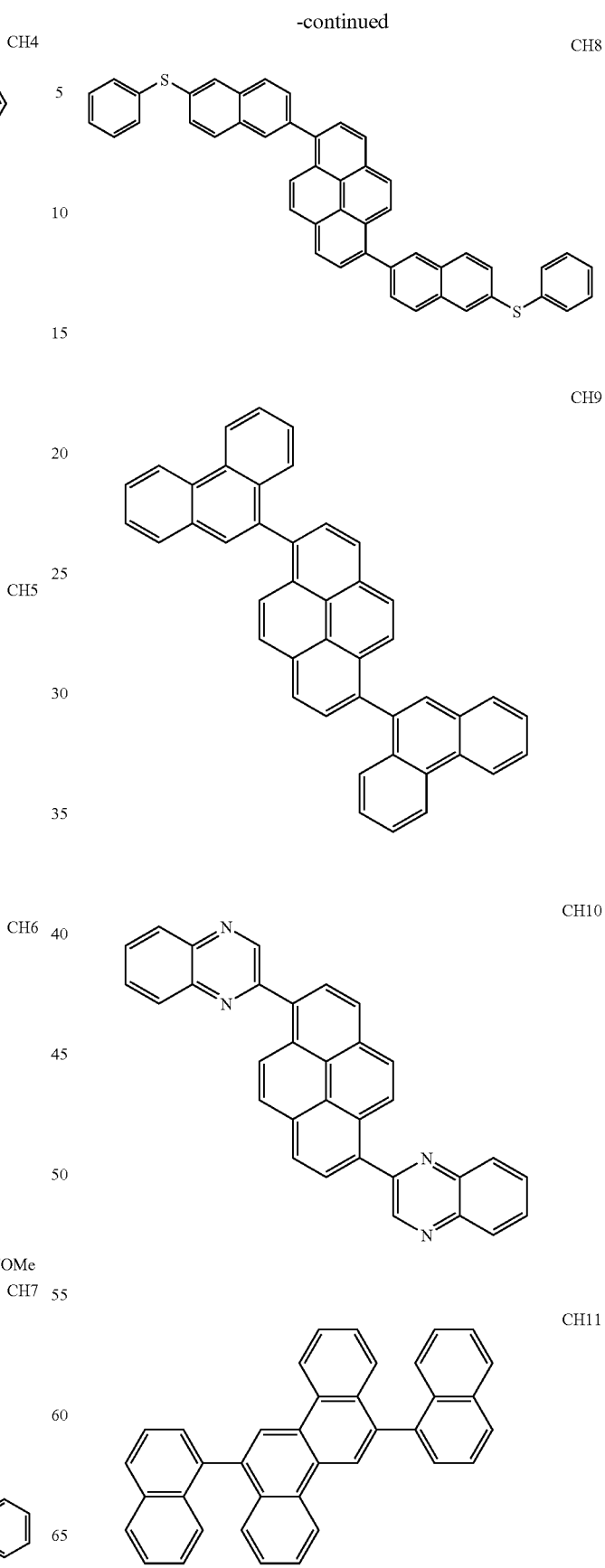
CH8
CH9
CH10
CH11

-continued
CH12
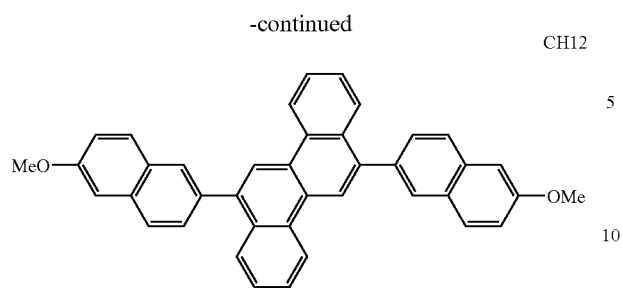
CH17
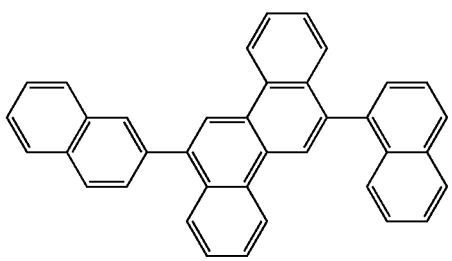
CH13
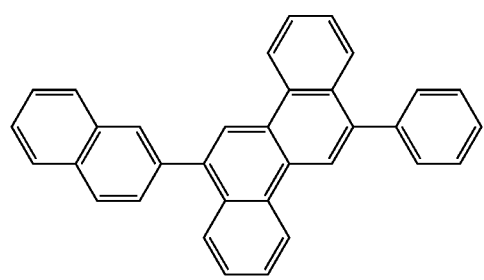
CH18
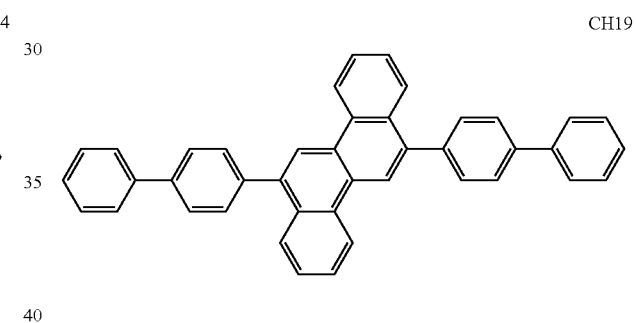
CH14
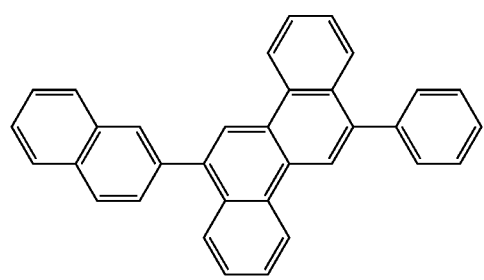
CH19
CH15
CH20
CH16
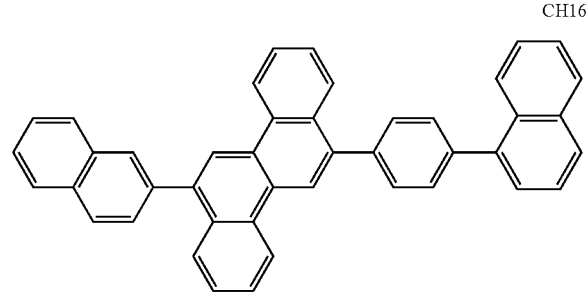
CH21
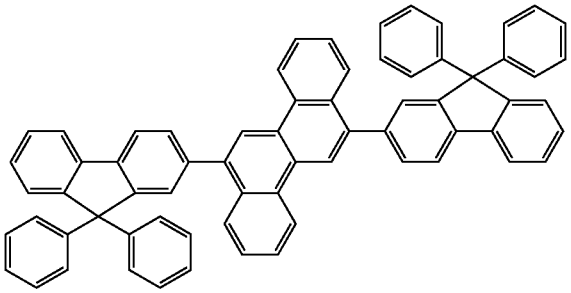

-continued
CH22
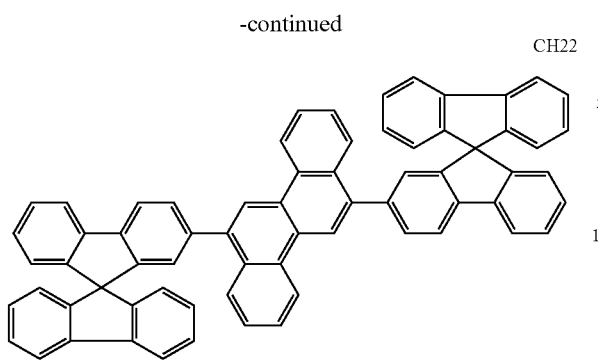
CH23
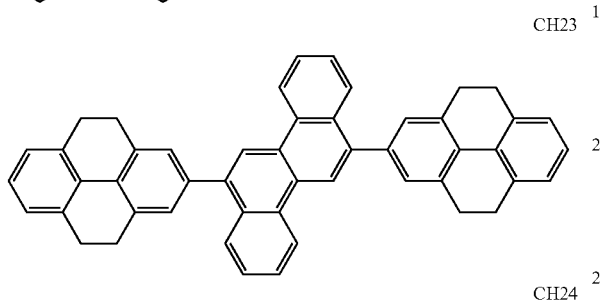
CH24
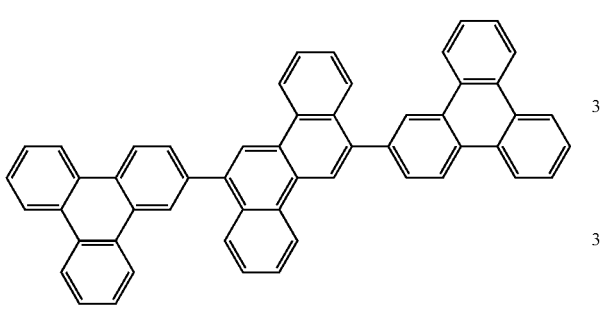
CH25
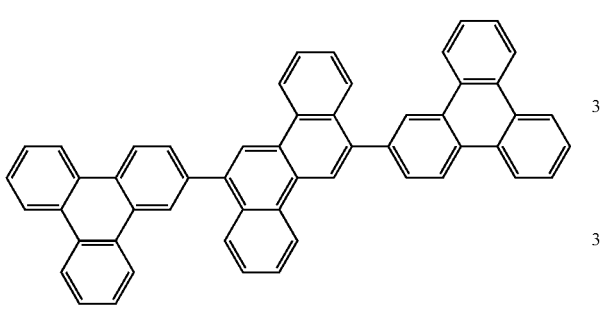
CH26
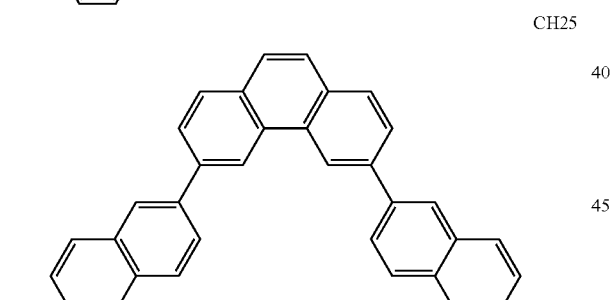
-continued
CH27
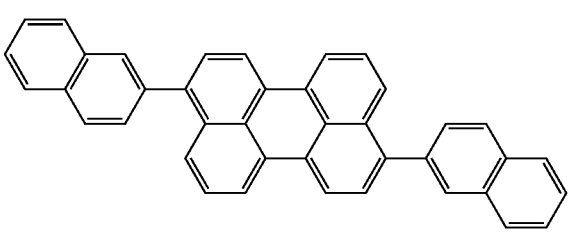
CH28
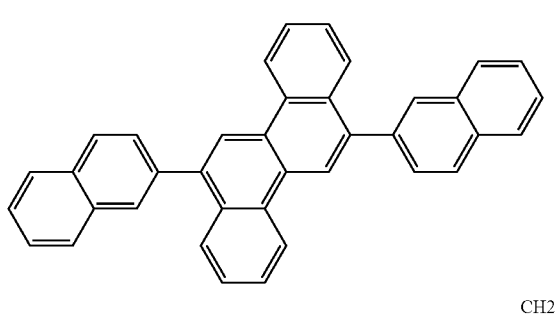
CH29
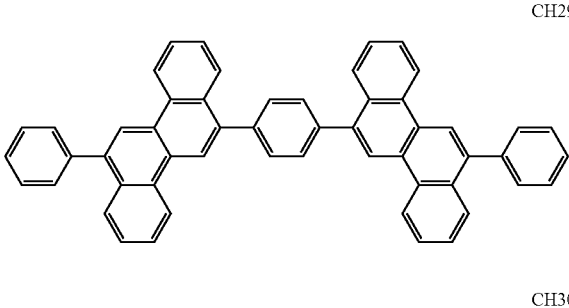
CH30
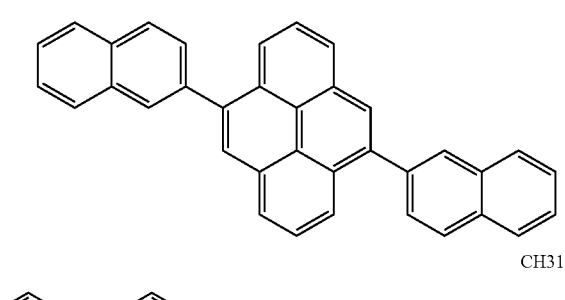
CH31
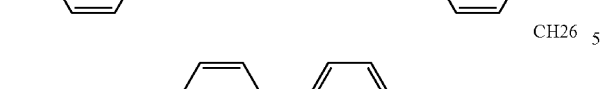
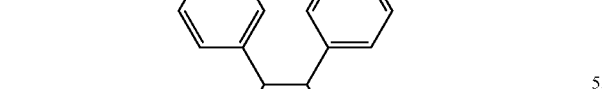
CH32
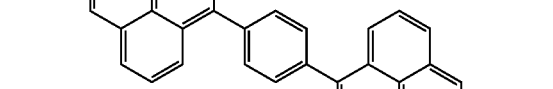

-continued

CH33

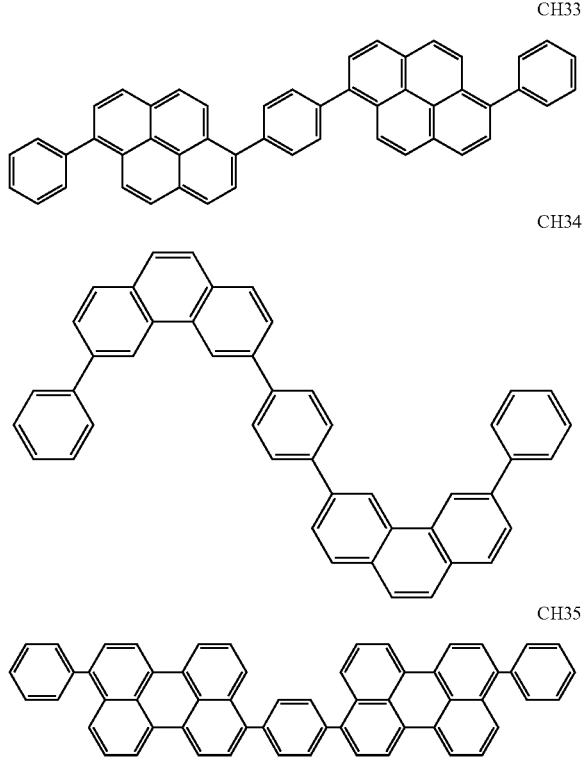

CH34

CH35

The oligoarylene derivative of the present invention is preferably used as a luminescent material and a hole transport material of organic EL devices.

The organic EL device of the present invention comprises a cathode, an anode and an organic thin film layer sandwiched between the cathode and the anode which is constituted of a single layer a plurality of layers including at least one luminescent layer wherein at least one layer of the organic thin film layer contains the oligoarylene derivative represented by any of the general formulae (1) to (4) as a single component or a component of a mixture.

The luminescent layer preferably contains the oligoarylene derivative represented by any of the general formulae (1) to (4), and more preferably the luminescent layer contains the oligoarylene derivative as a main component.

Also, in the organic EL device of the present invention, more preferably, the luminescent layer further contains an arylamine compound and/or a styrylamine compound.

Examples of the preferred styrylamine compound include those compounds represented by the following general formula (A):

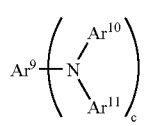
(A)

wherein $Ar^9$ is a group selected from the group consisting of phenyl, biphenyl, terphenyl, stilbene and distyrylaryl; $Ar^{10}$ and $Ar^{11}$ are respectively a hydrogen atom or a $C_6$ to $C_{20}$ aromatic group; $Ar^9$, $Ar^{10}$ and $Ar^{11}$ may be substituted; c is an integer of 1 to 4; and at least one of Ar10 and $Ar^{11}$ may be substituted with styryl.

Examples of the $C_6$ to $C_{20}$ aromatic group include phenyl, naphthyl, anthranyl, phenathryl and terphenyl.

Examples of the preferred arylamine compound include those compounds represented by the following formula (B):

(B)

wherein $Ar^{12}$ to $Ar^{14}$ are respectively a substituted or unsubstituted aryl group having 5 to 40 nuclear carbon atoms; and d is an integer of 1 to 4.

Examples of the aryl group having 5 to 40 nuclear carbon atoms include phenyl, naphthyl, anthranyl, phenanthryl, pyrenyl, coronyl, biphenyl, terphenyl, pyrrolyl, furanyl, thiophenyl, benzothiophenyl, oxadiazolyl, diphenylanthranyl, indolyl, carbazolyl, pyridyl, benzoquinolyl, fluoranthenyl, acenaphthofluoranthenyl and stilbene. Meanwhile, examples of the preferred substituent groups of these aryl groups include $C_1$ to $C_6$ alkyl groups such as ethyl, methyl, i-propyl, n-propyl, s-butyl, t-butyl, pentyl, hexyl, cyclopentyl and cyclohexyl, $C_1$ to $C_6$ alkoxy groups such as ethoxy, methoxy, i-propoxy, n-propoxy, s-butoxy, t-butoxy, pentoxy, hexyloxy, cyclopentoxy and cyclohexyloxy, aryl groups having 5 to 40 nuclear atoms, amino groups substituted with aryl groups having 5 to 40 nuclear atoms, ester groups substituted with aryl groups having 5 to 40 nuclear atoms, ester groups having a $C_1$ to $C_6$ alkyl group, cyano, nitro and halogen atoms.

The organic thin film layer may have a hole transport layer containing the oligoarylene derivative represented by any of the general formulae (1) to (4) as a single component or a component of a mixture, especially preferably as a main component thereof.

In the followings, the structure or configuration of the organic EL device according to the present invention is explained.

Typical structures of the organic EL device of the present invention are as follows.

(1) Anode/luminescent layer/cathode
(2) Anode/hole injection layer/luminescent layer/cathode
(3) Anode/luminescent layer /electron injection layer/cathode
(4) Anode/hole injection layer/luminescent layer/electron injection layer/cathode
(5) Anode/organic semiconductor layer/luminescent layer/cathode
(6) Anode/organic semiconductor layer/electron barrier layer/luminescent layer/cathode
(7) Anode/organic semiconductor layer/luminescent layer/adhesion modifying layer/cathode
(8) Anode/hole injection layer/hole transport layer/luminescent layer/electron injection layer/cathode
(9) Anode/insulating layer/luminescent layer/insulating layer/cathode
(10) Anode/inorganic semiconductor layer/insulating layer/luminescent layer/insulating layer/cathode
(11) Anode/organic semiconductor layer/insulating layer/luminescent layer/insulating layer/cathode
(12) Anode/insulating layer/hole injection layer/hole transport layer/luminescent layer/insulating layer/cathode

(13) Anode/insulating layer/hole injection layer/hole transport layer/luminescent layer/electron injection layer/cathode Among these structures, the structure (8) is usually preferably used though not particularly limited thereto.

The organic EL device is usually formed on a light-transmittable substrate. The light-transmittable substrate has a function of supporting the organic EL device, and preferably exhibits a light transmittance of 50% or more in a visible range of 400 to 700 nm. Further, the light-transmittable substrate usable in the present invention more preferably has a smooth surface.

Examples of the suitable light-transmittable substrate include a glass plate and a synthetic resin plate. Specific examples of the glass plate include plates made of soda lime glass, barium/strontium-containing glass, lead glass, aluminosilicate glass, borosilicate glass, barium borosilicate glass, quartz, etc. Specific examples of the synthetic resin plate include plates made of polycarbonate resins, acrylic resins, polyethylene terephthalate resins, polyether sulfide resins, polysulfone resins, etc.

Next, the anode is preferably made of electrode substances such as metals, alloys, electrically conductive compounds or mixtures thereof which have a large work function of 4 eV or more. Specific examples of the electrode substances for the anode include metals such as Au, and conductive materials such as CuI, ITO (indium tin oxide), $SnO_2$, ZnO and In—Zn—O. The anode may be produced by forming these electrode substances into a thin film by vapor deposition method or sputtering method. The anode preferably has such a property that when light emitted from the above luminescent layer is taken outside from the anode, a transmittance thereof relative to the emitted light is 10% or higher. Also, the anode preferably has a sheet resistance of several hundred $\Omega/\square$ or lower, and the thickness thereof may be selected from the range of usually from 10 nm to 1 μm and preferably from 10 to 200 nm though it varies depending upon the materials used therefor.

Next, the cathode is preferably made of electrode substances such as metals, alloys, electrically conductive compounds or mixtures thereof which have a small work function of 4 eV or lower. Specific examples of the electrode substances for the cathode include sodium, sodium-potassium alloy, magnesium, lithium, magnesium-silver alloy, aluminum/aluminum oxide, $Al/Li_2O$, $Al/LiO_2$, Al/LiF, aluminum, lithium alloys, indium and rare earth metals.

The cathode may be produced by forming these electrode substances into a thin film by vapor deposition method or sputtering method.

When light emitted from the luminescent layer is taken outside from the cathode, a transmittance thereof relative to the emitted light is preferably 10% or higher. Also, the cathode preferably has a sheet resistance of several hundred $\Omega/\square$ or lower, and the thickness of the cathode is usually from 10 nm to 1 μm and preferably from 50 to 200 nm.

In the organic EL device of the present invention, at least one of a pair of the thus produced electrodes is preferably provided on a surface thereof with a chalcogenide layer, a metal halide layer or a metal oxide layer (hereinafter, occasionally referred to merely as a "surface layer"). More specifically, the anode is provided on its surface facing the luminescent layer, with a layer made of chalcogenide (including an oxide) of metals such as silicon and aluminum, and the cathode is provided on its surface facing the luminescent layer, with a metal halide layer or a metal oxide layer. The provision of these surface layers ensures stable operation of the device.

Examples of the preferred chalcogenide include SiOx ($1 \leq X \leq 2$), AlOx ($1 \leq X \leq 1.5$), SiON and SiAlON. Examples of the preferred metal halide include LiF, $MgF_2$, $CaF_2$ and fluorinated rare earth metals. Examples of the metal oxide include $Cs_2O$, $Li_2O$, MgO, SrO, BaO and CaO.

Further, in the organic EL device of the present invention, at least one of a pair of the thus produced electrodes is preferably provided on a surface thereof with a mixed region composed of an electron transport compound and a reducing dopant, or a mixed region composed of a hole transport compound and an oxidizing dopant. With such an arrangement, the electron transport compound tends to be reduced into anions, so that electrons tend to be injected and transported from the mixed region into the luminescent layer. In addition, since the hole transport compound tends to be oxidized into cations, so that holes tend to be injected and transported from the mixed region into the luminescent layer. Examples of the preferred oxidizing dopant include various Lewis acids and acceptor compounds. Examples of the preferred reducing dopant include alkali metals, alkali metal compounds, alkali earth metals. rare earth metals and compounds thereof.

In the organic EL device of the present invention, the luminescent layer has:

(1) Injection function: function capable of injecting holes from the anode or hole injection layer, or injecting electrons from the cathode or electron injection layer, upon application of an electric filed thereto;

(2) Transport function: function capable of moving the injected electric charges (electrons and holes) by a force of the electric field applied; and (3) Luminescent function: function capable of providing a site for recombination between the electrons and holes which leads to light emission.

The luminescent layer may be formed by conventionally known methods such as vapor deposition method, spin-coating method and LB method. The luminescent layer is more preferably made of a molecular deposition film. Here, the "molecular deposition film" means a thin film deposited from a material compound in the form of a gas phase, or a film solidified from a material compound in the form of a solution or a liquid phase. The molecular deposition film is usually distinguished from those thin films formed by LB method (molecular accumulation films) owing to the difference in coagulated structure and higher-order structure as well as the difference in functions due to these structures.

In addition, as described in Japanese Patent Application Laid-open No. Sho 57(1982)-51781, the luminescent layer may also be produced by dissolving a binder such as resins and the material compound in a solvent and then forming the resultant solution into a thin film by a spin-coating method, etc.

In the present invention, the luminescent layer may contain, in addition to the above luminescent material made of the oligoarylene derivative of the present invention, other known luminescent materials, if desired, unless the addition of these materials adversely affects the objects of the present invention. Alternatively, a luminescent layer containing the other known luminescent materials may be laminated on the luminescent layer made of the luminescent material containing the oligoarylene derivative of the present invention.

Next, the hole injection/transport layer serves for aiding injection of holes into the luminescent layer and transporting the injected holes up to a light emission region, and has a large hole mobility and an ionization energy as small as usually 5.5 eV or less. The hole injection/transport layer is preferably made of a material capable of transporting holes into the luminescent layer at a lower field intensity, and more preferably such a material having, for example, a hole mobility of at least $10^{-6}$ cm$^2$/V·s upon application of an electric field of $10^4$ to $10^6$ V/cm. As such a hole transport material, there may be usefully used the oligoarylene derivative of the present invention. In addition, the hole transport material may be optionally selected from those ordinarily used as a transport material for electric charge, i.e., holes among conventional photoconductive materials, as well as known materials used for a hole injection layer of organic EL devices.

The hole injection/transport layer may be produced by forming the hole injection/transport material into a thin film by known methods such as, for example, vapor deposition method, spin-coating method, casting method and LB method. In this case, the thickness of the hole injection/transport layer is not particularly limited, and usually in the range of 5 nm to 5 μm.

The electron injection/transport layer serves for aiding injection of electrons into the luminescent layer and transporting the injected electrons up to the light emission region, and has a large electron mobility. Further, the adhesion modifying layer may be made of a material having a good adhesion to especially the cathode among the electron injection materials. Examples of the suitable material used for the electron injection layer include 8-hydroxyquinoline and metal complexes of derivatives thereof. Specific examples of 8-hydroxyquinoline and metal complexes of derivatives thereof include metal chelate oxinoid compounds containing a chelate of oxine such as, generally, 8-quinolinol and 8-hydroxyquinoline. For example, tris(8-quinolinol)aluminum may be used as the electron injection material.

Also, in general, the organic EL device tends to suffer from defects of pixels due to leakage or short since an electric field is applied to the ultra-thin film. In order to prevent this problem, a pair of a thin insulating layer may be inserted between the pair of electrodes.

Examples of materials for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. These materials may be used in the form of a mixture or a laminate of any two or more thereof.

Then, the organic EL device of the present invention may be produced, for example, by forming the anode and the luminescent layer together with the hole injection layer and the electron injection layer, if required, and then finally forming the cathode, using the above materials and methods. Alternatively, the organic EL device may be produced in the reverse order starting from formation of the cathode and terminating at formation of the anode.

In the followings, the production of the organic EL device formed on a light-transmittable substrate which is successively provided with an anode, a hole injection layer, a luminescent layer, an electron injection layer and a cathode is explained.

First, a thin film made of an anode material is formed on an appropriate light-transmittable substrate by a vapor deposition method or a sputtering method such that the thickness thereof is 1 μm or lower and preferably 10 to 200 nm to thereby form an anode. Next, a hole injection layer is formed on the anode. The hole injection layer may be formed by the above-mentioned vacuum deposition method, spin-coating method, casting method or LB method. Of these methods, the vacuum deposition method is preferred since this method provides a uniform film that is free from defects such as occurrence of pinholes. In the case where the hole injection layer is formed by the vacuum deposition method, the deposition conditions may vary depending upon compounds (materials for the hole injection layer) used, crystal structure or recombination structure of the aimed hole injection layer, etc. In general, the deposition conditions are preferably selected such that the deposition source temperature is 50 to 450° C., the vacuum degree is $10^{-7}$ to $10^{-3}$ torr, the deposition velocity is 0.01 to 50 nm/s, the substrate temperature is −50 to 300° C., and the thickness of layer to be deposited is 5 nm to 5 μm.

Then, a luminescent layer is formed on the hole injection layer. The luminescent layer may be produced from the luminescent material of the present invention, specifically may also be produced by forming the luminescent material into a thin film by vacuum deposition method, spin-coating method, casting method or the like. Of these methods, the vacuum deposition method is preferred since this method provides a uniform film that is free from defects such as occurrence of pinholes. In the case where the luminescent layer is formed by the vacuum deposition method, the deposition conditions may vary depending upon compounds used. In general, the deposition conditions are preferably selected from the same ranges as used upon formation of the hole injection layer. The thickness of the luminescent layer is preferably 10 to 40 nm.

Next, an electron injection layer is formed on the luminescent layer. The electron injection layer is also preferably formed by the vacuum deposition method for providing a uniform film similarly to the formation of the hole injection layer and the luminescent layer. The deposition conditions may be selected from the same ranges as used upon formation of the hole injection layer and the luminescent layer.

Finally, a cathode is laminated on the electron injection layer to obtain the organic EL device. The cathode is made of metal and may be formed by vacuum deposition method or sputtering method. Of these methods, the vacuum deposition method is preferred in order to prevent damage to the underlying organic substance layer upon formation of the film.

The production of the organic EL device including the step of forming the anode up to the step of forming the cathode is preferably completed by one vacuum drawing stroke.

When a D.C. voltage is applied to the organic EL device, the anode is connected to a positive (+) polarity and the cathode is connected to a negative polarity (−) and a voltage of 3 to 40 V is applied therebetween, so that light is emitted from the organic EL device. On the contrary, even though the anode is connected to a negative polarity (−) and the cathode is connected to a positive (+) polarity, no light is emitted from the organic EL device. Further, in the case where an alternating current is applied to the anode and cathode, light emission is observed only when the anode is a positive (+) polarity and the cathode is a negative polarity (−). The alternating current applied may have an optional waveform.

The present invention will be described in more detail by reference to the following examples. However, it should be noted that the following examples are only illustrative and not intended to limit the invention thereto.

EXAMPLE 1

SYNTHESIS OF 2,6-bis(2-naphthyl)pyrene (CH1)

Under an argon atmosphere, 3 g of 2,6-dibromopyrene, 3.6 g of 2-naphthaleneboric acid available from Tokyo Kasei Co., Ltd., and 0.36 g of tetrakis(triphenylphosphine)palladium (0) available from Hiroshima Wako Co., Ltd., were dissolved in 100 mL of toluene. The resultant solution was mixed with a solution prepared by dissolving 5 g of sodium carbonate in 24 mL of water, and the mixed solution was refluxed for 10 h and allowed to stand over one night.

The obtained reaction mixture was filtered and then successively washed with water, methanol and acetone, thereby obtaining 2.9 g of a light-yellow solid.

As a result of the measurement for FD-MS (field desorption mass analysis) of the obtained compound, it was confirmed that m/z=454 was obtained relative to $C_{36}H_{22}$=454, and, therefore, the compound was identified to be 2,6-bis(2-naphthyl)pyrene (CH1) (yield: 77%).

EXAMPLE 2

SYNTHESIS OF 6,12-bis(1-naphthyl)chrysene (CH2)

Under an argon atmosphere, 3 g of 6,12-dibromochrysene, 4 g of 1-naphthaleneboric acid available from Tokyo Kasei Co., Ltd., and 0.36 g of tetrakis(triphenylphosphine)palladium (0) available from Hiroshima Wako Co., Ltd., were dissolved in 100 mL of toluene. The resultant solution was mixed with a solution prepared by dissolving 5 g of sodium carbonate in 24 mL of water, and the resultant mixed solution was refluxed for 10 h and allowed to stand over one night.

The obtained reaction mixture was filtered and then successively washed with water, methanol and acetone, thereby obtaining 3.2 g of a light-yellow solid.

As a result of the measurement for FD-MS of the obtained compound, it was confirmed that m/z=480 was obtained relative to $C_{38}H_{24}$=480, and, therefore, the compound was identified to be 6,12-bis(1-naphthyl)chrysene (CH2) (yield: 85%).

EXAMPLE 3

SYNTHESIS OF 6,12-bis(9-phenathryl)chrysene (CH3)

Under an argon atmosphere, 3 g of 6,12-dibromochrysene, 5 g of 9-phenathreneboric acid available from Tokyo Kasei Co., Ltd., and 0.36 g of tetrakis(triphenylphosphine)palladium (0) available from Hiroshima Wako Co., Ltd., were dissolved in 100 mL of toluene. The resultant solution was mixed with a solution prepared by dissolving 5 g of sodium carbonate in 24 mL of water, and the resultant mixed solution was refluxed for 10 h and allowed to stand over one night.

The obtained reaction mixture was filtered and then successively washed with water, methanol and acetone, thereby obtaining 4.2 g of a light-yellow solid.

As a result of the measurement for FD-MS of the obtained compound, it was confirmed that m/z=580 was obtained relative to $C_{46}H_{28}$=580, and, therefore, the compound was identified to be 6,12-bis(9-phenathryl)chrysene (CH3) (yield: 93%).

EXAMPLE 4

SYNTHESIS OF 6,12-bis(2-terphenyl)chrysene (CH4)

Under an argon atmosphere, 3 g of 6,12-dibromochrysene, 5 g of 2-terphenylboric acid and 0.36 g of tetrakis(triphenylphosphine)palladium (0) available from Hiroshima Wako Co., Ltd., were dissolved in 100 mL of toluene. The resultant solution was mixed with a solution prepared by dissolving 5 g of sodium carbonate in 24 mL of water, and the resultant mixed solution was refluxed for 10 h and allowed to stand over one night.

The obtained reaction mixture was filtered and then successively washed with water, methanol and acetone, thereby obtaining 4.2 g of a light-yellow solid.

As a result of the measurement for FD-MS of the obtained compound, it was confirmed that m/z=684 was obtained relative to $C_{54}H_{36}$=684, and, therefore, the compound was identified to be 6,12-bis(2-terphenyl)chrysene (CH4) (yield: 79%).

EXAMPLE 5

Production of Organic EL Device

A glass substrate with an ITO transparent electrode having a size of 25 mm×75 mm×1.1 mm in thickness which was available from Geomatic Co., Ltd., was subjected to ultrasonic cleaning for 5 min in isopropyl alcohol, and then to UV ozone cleaning for 30 min. The thus cleaned glass substrate with transparent electrode lines was fitted to a substrate holder of a vacuum deposition apparatus. First, a 60 nm-thick film made of the below-mentioned N,N'-bis(N,N'-diphenyl-4-aminophenyl)-N,N-diphenyl-4,4'-diamino-1,1'-biphen yl (hereinafter referred to merely "TPD232 film") was formed on a surface of the glass substrate on which the transparent electrode lines were formed, such that the transparent electrode was covered therewith. The thus formed TPD232 film had a function as a hole injection layer. Successively, a 20 nm-thick film made of the below-mentioned N,N,N',N'-tetra (4-biphenyl)diaminobiphenylene (hereinafter referred to merely as "TBDB film") was formed on the TPD232 film. The thus obtained TBDB film had a function as a hole transport layer. Further, CH1 as a luminescent material (host material) was vapor-deposited on the TBDB film to form a 40 nm-thick CH1 film, and at the same time, the below-mentioned styryl-containing amine compound D1 as a luminescent molecule (dopant) was vapor-deposited thereon at a weight ratio of CH1 to D1 of 40:2. The thus formed deposited film had a function as a luminescent layer. Then, a 10 nm-thick film made of the below-mentioned Alq was formed on the luminescent layer. The thus formed Alq film had a function as an electron injection layer. Thereafter, Li as a reducing dopant (Li source available from SAES Getter S.p.A.) and Alq were subjected to binary vapor deposition to form an Alq:Li film having a thickness of 10 nm as an electron injection layer (cathode). Then, metallic Al was vapor-deposited on the Alq:Li film to form a metal cathode, thereby producing an organic EL device.

The thus obtained organic EL device was subjected to measurement of its luminous efficiency near a luminance of 100 nit. The results are shown in Table 1.

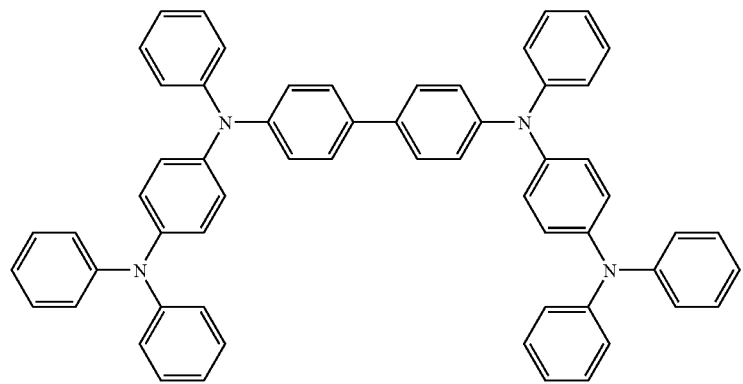
TPD232
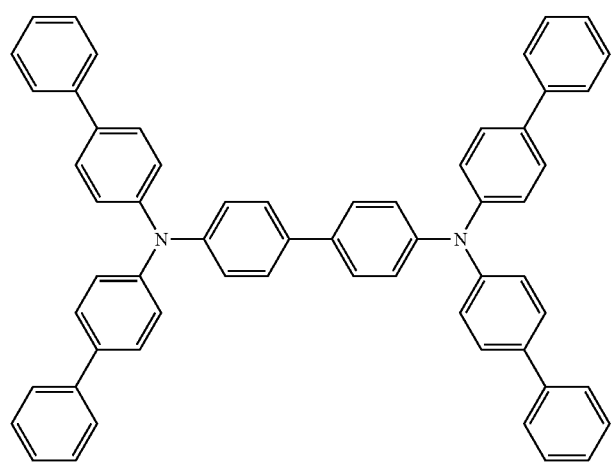
TBDB
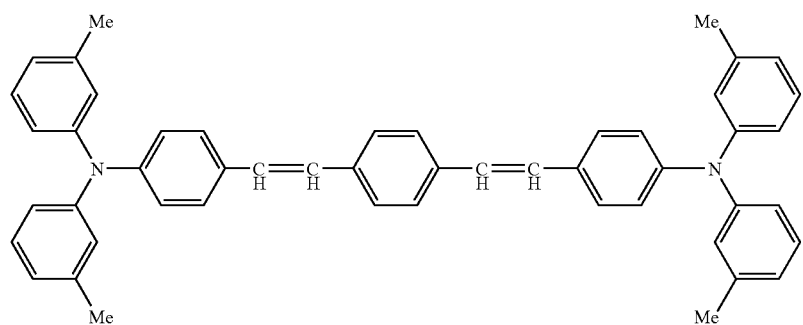
D1
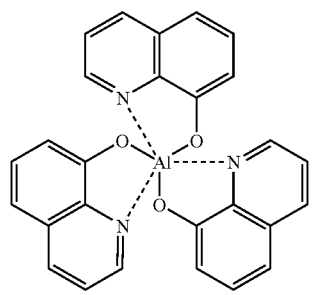
Alq

EXAMPLE 6

Production of Organic EL Device

The same procedure as in EXAMPLE 5 was repeated except for using the below-mentioned aromatic amine D2 as a dopant instead of the styryl-containing amine compound D1, thereby producing an organic EL device. The obtained organic EL device was subjected to measurement of its luminous efficiency. The results are shown in Table 1.

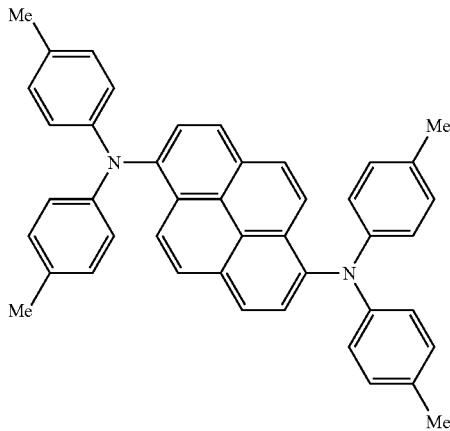

D2

EXAMPLES 7 TO 12

Production of Organic EL Device

The same procedure as in EXAMPLE 5 was repeated except for using the host material and the dopant as shown in Table 1, thereby producing an organic EL device. The obtained organic EL device was subjected to measurement of its luminous efficiency. The results are shown in Table 1.

COMPARATIVE EXAMPLE 1

Production of Organic EL Device

The same procedure as in EXAMPLE 5 was repeated except for using the below-mentioned compound an1 as a host material instead of CH1, thereby producing an organic EL device. The obtained organic EL device was subjected to measurement of its luminous efficiency. The results are shown in Table 1.

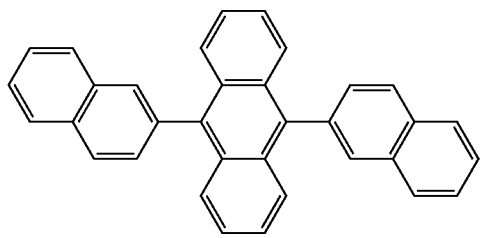

an1

COMPARATIVE EXAMPLE 2

Production of Organic EL Device

The same procedure as in COMPARATIVE EXAMPLE 1 was repeated except for using the aromatic amine D2 as a dopant instead of the styryl-containing amine compound D1, thereby producing an organic EL device. The obtained organic EL device was subjected to measurement of its luminous efficiency. The results are shown in Table 1.

TABLE 1

| Luminescent layer | | Luminous efficiency | Color of |
|---|---|---|---|
| Host material | Dopant | (cd/A) | emitted light |
| Example 5 | CH1 | D1 | 11.1 | Blue |
| Example 6 | CH1 | D2 | 11.5 | Blue |
| Example 7 | CH2 | D1 | 10.5 | Blue |
| Example 8 | CH2 | D2 | 10.7 | Blue |
| Example 9 | CH3 | D1 | 10.2 | Blue |
| Example 10 | CH3 | D2 | 10.4 | Blue |
| Example 11 | CH4 | D1 | 10.3 | Blue |
| Example 12 | CH4 | D2 | 10.6 | Blue |
| Comparative Example 1 | an1 | D1 | 9.0 | Blue |
| Comparative Example 2 | an1 | D2 | 9.3 | Blue |

As shown in Table 1, it was confirmed that the organic EL devices obtained in Examples 5 to 12 emitted blue light at a higher luminous efficiency as compared to those obtained in Comparative Examples 1 and 2.

INDUSTRIAL APPLICABILITY

As described above, the organic EL device made by using the oligoarylene derivative according to the present invention can emit blue light at a high luminous efficiency. Therefore, the organic EL device of the present invention is useful as a full-color organic EL device.

The invention claimed is:

1. An oligoarylene derivative, wherein the oligoarylene derivative is selected from the group consisting of the following compounds designated CH2, CH3, CH4, CH11, CH13, CH14, CH16, CH17, CH18, CH19, CH20, CH21, CH22, CH23, and CH24:

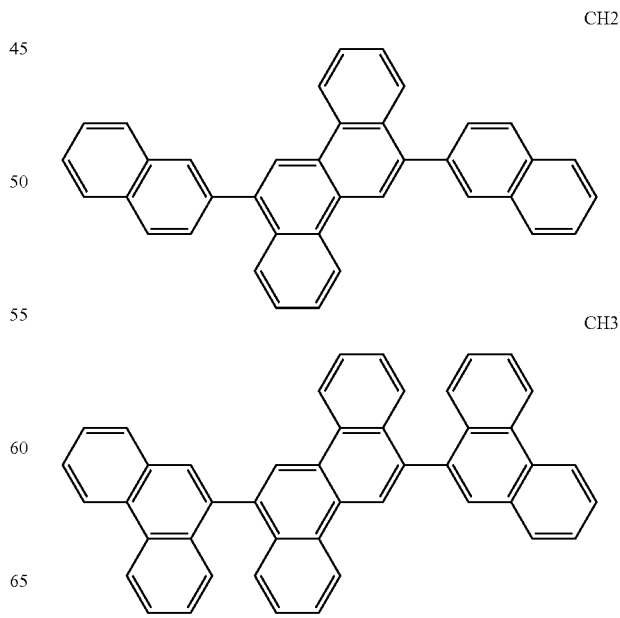

-continued
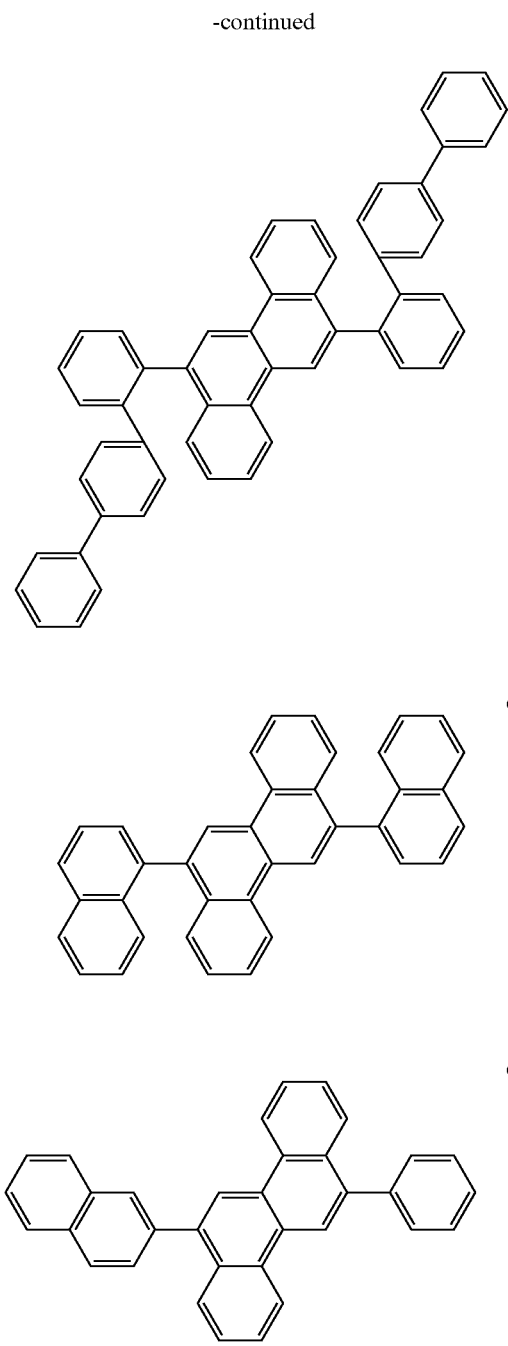
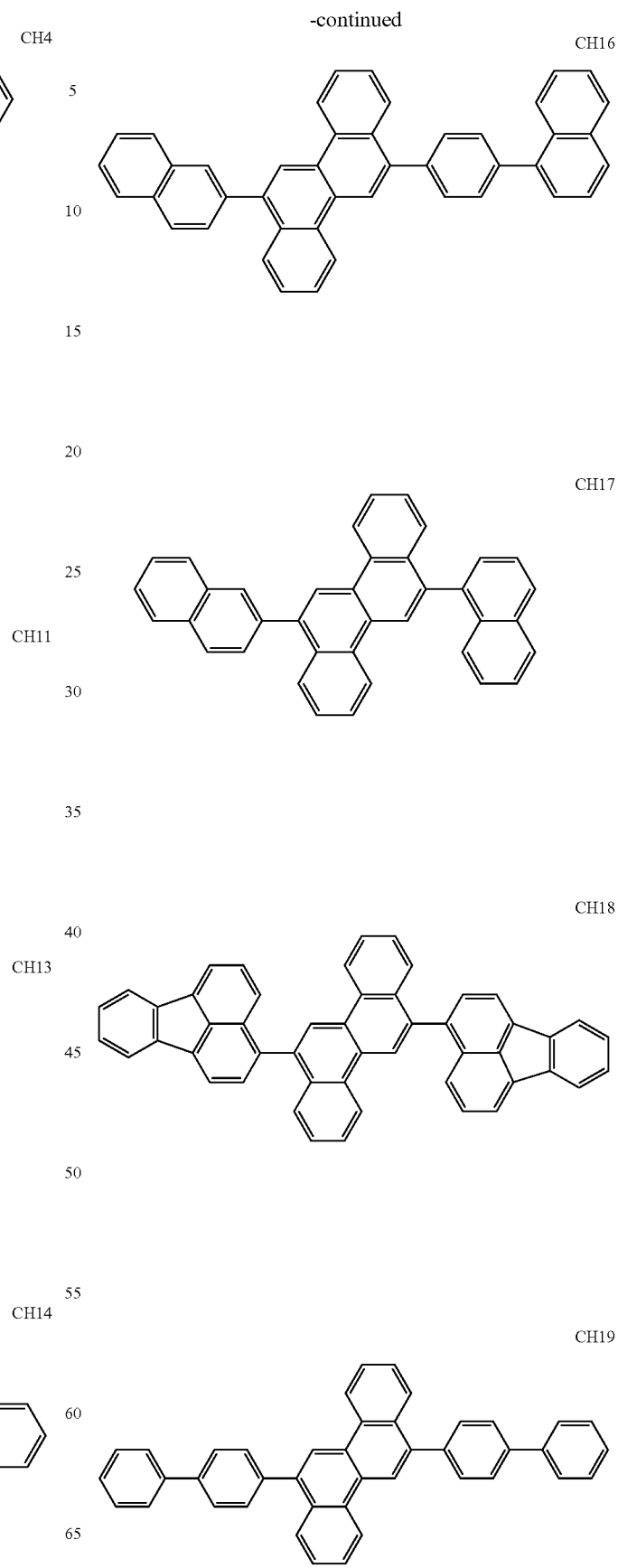

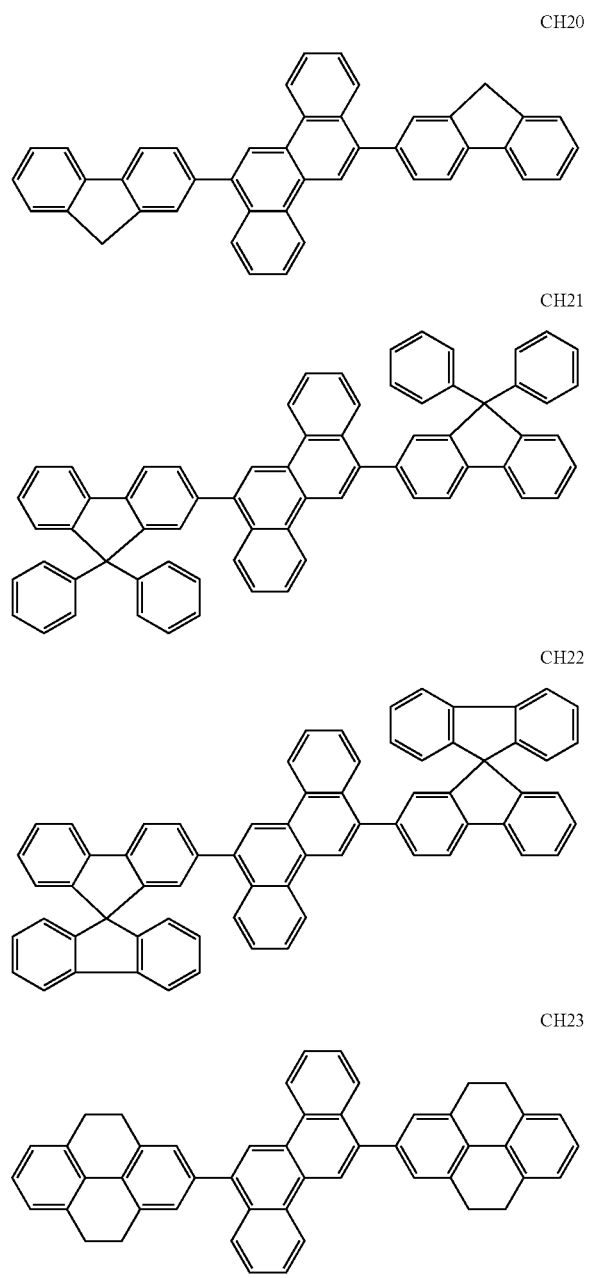

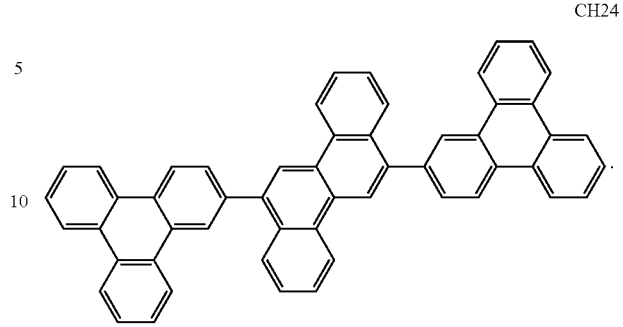

2. The oligoarylene derivative according to claim 1, wherein the oligoarylene derivative is a luminescent material for organic electroluminescent devices.

3. The oligoarylene derivative according to claim 1, wherein the oligoarylene derivative is a hole transport material for organic electroluminescent devices.

4. An organic electroluminescent device comprising a cathode, an anode, and an organic thin film layer sandwiched between the cathode and the anode,
said organic thin film layer comprising a single layer or a plurality of layers which includes at least one luminescent layer, wherein at least one layer of the organic thin film layer contains the oligoarylene derivative of claim 1.

5. The organic electroluminescent device according to claim 4, wherein the luminescent layer contains the oligoarylene derivative.

6. The organic electroluminescent device according to claim 4, wherein the luminescent layer mainly contains the oligoarylene derivative.

7. The organic electroluminescent device according to claim 4, wherein the luminescent layer further contains an arylamine compound.

8. The organic electroluminescent device according to claim 4, wherein the luminescent layer further contains an styrylamine compound.

9. The organic electroluminescent device according to claim 4, wherein the organic thin film layer comprises a hole transport layer containing the oligoarylene derivative.

10. The organic electroluminescent device according to claim 9, wherein the hole transport layer mainly contains the oligoarylene derivative.

11. The organic electroluminescent device according to claim 4, wherein the organic electroluminescent device is capable of emitting a blue light.

* * * * *